(12) United States Patent
Vogt et al.

(10) Patent No.: US 8,236,569 B2
(45) Date of Patent: Aug. 7, 2012

(54) MULTI-DIMENSIONAL INTEGRATED DETECTION AND ANALYSIS SYSTEM (MIDAS) BASED ON MICROCANTILVERS

(75) Inventors: Tom Vogt, Chapin, SC (US); Gautam Koley, Columbia, SC (US)

(73) Assignee: University of South Carolina, Columbia, SC (US)

( * ) Notice: Subject to any disclaimer, the term of this patent is extended or adjusted under 35 U.S.C. 154(b) by 995 days.

(21) Appl. No.: 12/187,845

(22) Filed: Aug. 7, 2008

(65) Prior Publication Data

US 2012/0171775 A1 Jul. 5, 2012

Related U.S. Application Data

(60) Provisional application No. 60/963,780, filed on Aug. 7, 2007.

(51) Int. Cl.
*G01N 27/22* (2006.01)
(52) U.S. Cl. .................. 436/151; 436/149; 436/116
(58) Field of Classification Search .................. None
See application file for complete search history.

(56) References Cited

U.S. PATENT DOCUMENTS

2005/0074871 A1 * 4/2005 Albert et al. ............... 435/287.2

OTHER PUBLICATIONS

Henritte Jensenious, Ph.D. Thesis "Microcantilever-based studies of bio/chemical systems", Mar. 15, 2002, Mikroelektronik Centret, Technical University of Denmark, Lyngby, Denmark.*
Vasudev "Microcantilever-Based Sensors", NNIN REU 2006 Research Accomplishments o Mechanical Devices, pp. 98-99.*
Sandeep Kumar Vashist "A Review of Microcantilevers for Sensing Applications" Journal of Nanotechnology Online, 2007, v. 3, Issue: June, pp. 1-15.*
Qazi and Koley "NO2 Detection Using Microcantilever Based Potentiometry", Sensors, 2008, v. 8, pp. 7144-7156.*

* cited by examiner

*Primary Examiner* — Yelena G Gakh
(74) *Attorney, Agent, or Firm* — Dority & Manning, P.A.

(57) ABSTRACT

The present invention is a multidimensional integrated detection and analysis system (MIDAS) for any gas or fluid that transfers or accepts electronic charge (including but not limited to $CH_4$, $CO_2$, CO, $NO_x$, $SO_x$, $H_2O$, $NH_3$, $NH_x$). MIDAS allows for the development of a highly sensitive, selective, and expedient sensor platform capable of uniquely identifying adsorbed molecules based on simultaneous measurement of truly orthogonal responses based on work function ($\phi$), capacitance (C), and/or conductance ($\sigma$) changes.

17 Claims, 6 Drawing Sheets

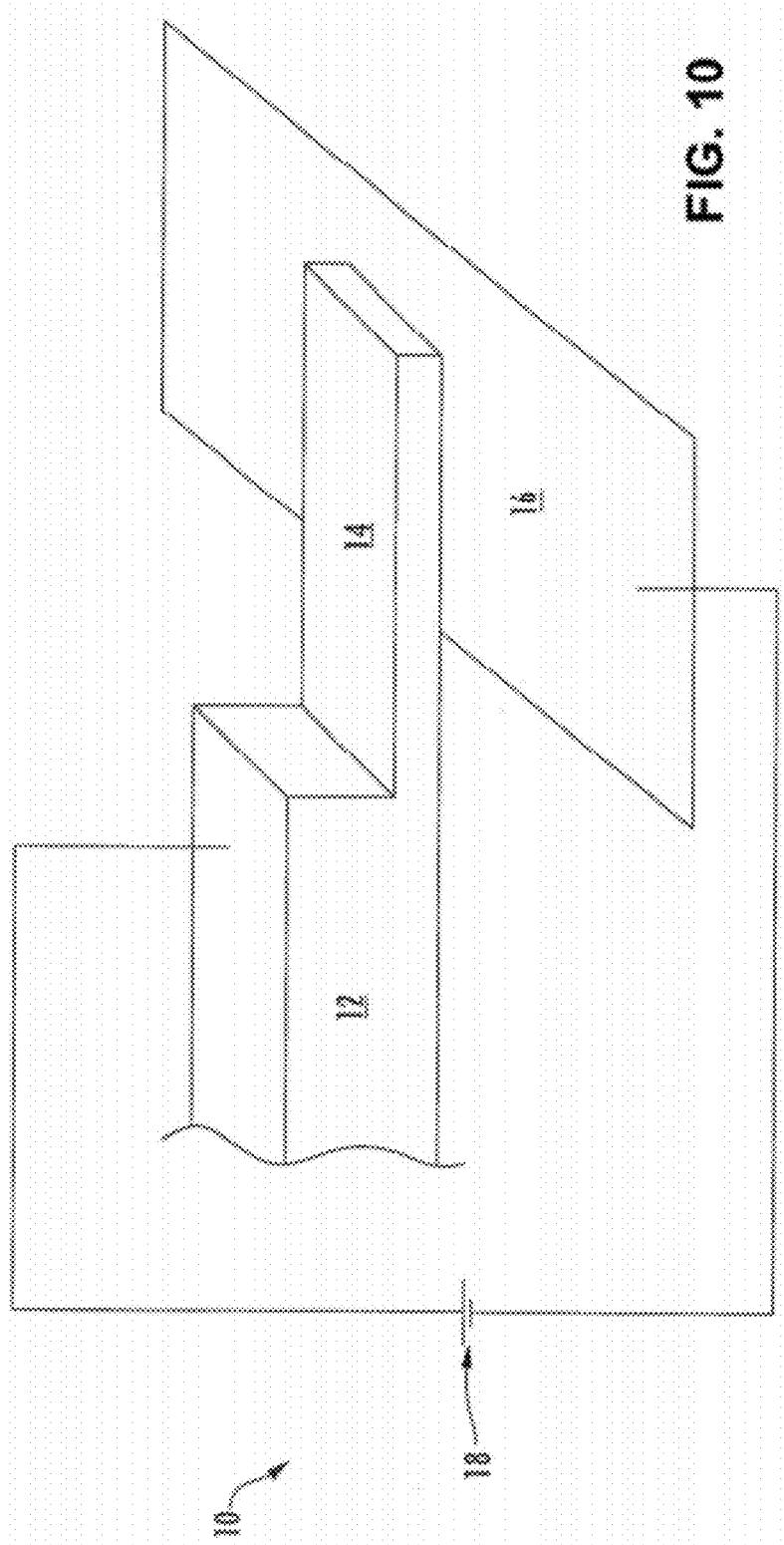

MULTI-DIMENSIONAL INTEGRATED DETECTION AND ANALYSIS SYSTEM (MIDAS) BASED ON MICROCANTILVERS

RELATED APPLICATIONS

The present application claims priority to U.S. Provisional Patent Application Ser. No. 60/963,780 filed on Aug. 7, 2007 titled "Multi-Dimensional Integrated Detection and Analysis System (MIDAS)", the disclosure of which is incorporated by reference herein.

BACKGROUND

Accurate and expedient detection of target molecules (e.g. chemical warfare agents, explosives, pollutant gases, and other analytes, etc.) is of paramount importance from the perspectives of defense, homeland security, counter-terrorism, and a large variety of industrial and civilian applications. In general, unique detection and identification of target molecules can be performed by separation followed by quantization based on one of their unique physical properties, such as, ion mobility, diffusivity, charge/mass ratio in ionic form or unique signatures such as infrared (IR) absorption spectra. Instruments such as ion-mobility spectrometers, gas chromatographs, mass spectrometers, and IR spectrometers exploit these physical properties to uniquely detect target molecules. In spite of the accuracy and reliability of these "physics-based" detection systems, they are more suitable for laboratory measurements rather than in-situ sensing, because of their larger dimensions, weight, power consumption, and cost.

In recent years, research efforts have been directed toward miniaturizing these systems with an aim to mitigate the above-mentioned drawbacks. However, they are still not suitable for a wide variety of applications including remote operations, distributed and networked sensor systems, and many in-situ applications (e.g., inside the human body, oil-fields, or space applications), where smaller dimensions and weights as well as low power consumptions are extremely critical. In addition, any integration with modern day microfabricated devices is not very feasible at present. Responding to the challenges faced by "physics-based" sensors, research efforts have been directed toward developing sensors utilizing modern microfabrication techniques and nanotechnology. A majority of these sensors are based on changes in their electronic, optical, or mechanical properties caused by adsorption of target molecules at the surface. Typical examples include a chem-FET type sensor, where the change in drain current caused is measured, a fluorescent polymer based sensor where the fluorescence is changed by the presence of certain molecules, or a microcantilever based sensor, where the change in static deflection caused by a change in surface stress is measured. Recent research by the present inventors has resulted in a detection technique based on adsorption induced changes in surface work function (SWF) using resonant microcantilevers.

The miniaturized sensor devices currently used perform detection based on changes in only a single parameter, i.e. conductance for commonly used amperometric sensors or stress change for static cantilever based sensors. However, these single parameters are affected by the concentration as well as the nature of the molecules, which makes it extremely difficult to uniquely identify the type of molecules as well as quantify their concentration. In general, there are two approaches to address this problem: (i) by using an appropriate functionalization layer on the active surface of the transducer to obtain selective response from a target molecular species, and (ii) by using an "artificial nose" type technique to obtain n-dimensional signature of the analyte molecular species from an array of non-selective (but broadly sensitive) functionalization layers, which can be analyzed using classification schemes such as, Principal Component Analysis (PCA), Linear Discrimination analysis (LDA), etc. or several variations of Artificial Neural Networks (ANN). These detection strategies are shown schematically in FIG. 1.

Although the first approach increases the specificity of detection, with the exception of certain bio-molecular interactions (such as between antibodies and antigens), the functionalization layers are not entirely specific (or may be even non-existent for a given molecule). Hence, different types of related molecular species, or their mixture, can produce a significant sensor response, especially when their concentrations are relatively higher. This can result in a large false positive rate. The second approach is more suited for classification of a given molecular species (or mixture of several species) based on a-priori analysis and training of an exactly similar species. However, even with an array of functionalization layers, and sophisticated classification schemes, uncertainties in molecular detection are high, and quantitative analysis of a mixture with multiple molecular species remains a major challenge. In particular, degradation of response and partial poisoning can pose a very significant challenge for detection based on one-dimensional responses. Also, real time analysis is very difficult using this technique.

The present invention, a novel multidimensional integrated detection and analysis system and method, seeks to overcome the disadvantages presented by these prior art construction and methods.

SUMMARY OF INVENTION

The present invention is a novel Multidimensional Integrated Detection and Analysis System (MIDAS) which leads to the development of robust, versatile, and inexpensive sensors based on a nanostructured graphite and/or graphene functionalization layer that can be put very easily and economically on a variety of substrates. The system uniquely integrates potentiometric and capacitive detection techniques with the commonly used amperometric technique for highly sensitive, expedient, and accurate detection of target molecules. The system uniquely identifies molecules based on extraction of novel orthogonal multi-dimensional signatures, with capability to analyze mixtures in real time. The system also significantly improves the response time, sensitivity, and false identification rate when the sensing paradigm is applied to existing systems such as the "Electronic Nose."

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which:

FIG. 10 depicts a side view of the exemplary detection system of FIG. 9.

DETAILED DESCRIPTION OF INVENTION

It is to be understood by one of ordinary skill in the art that the present discussion is a description of exemplary embodiments only, and is not intended as limiting the broader aspects of the present invention.

Figure 1:
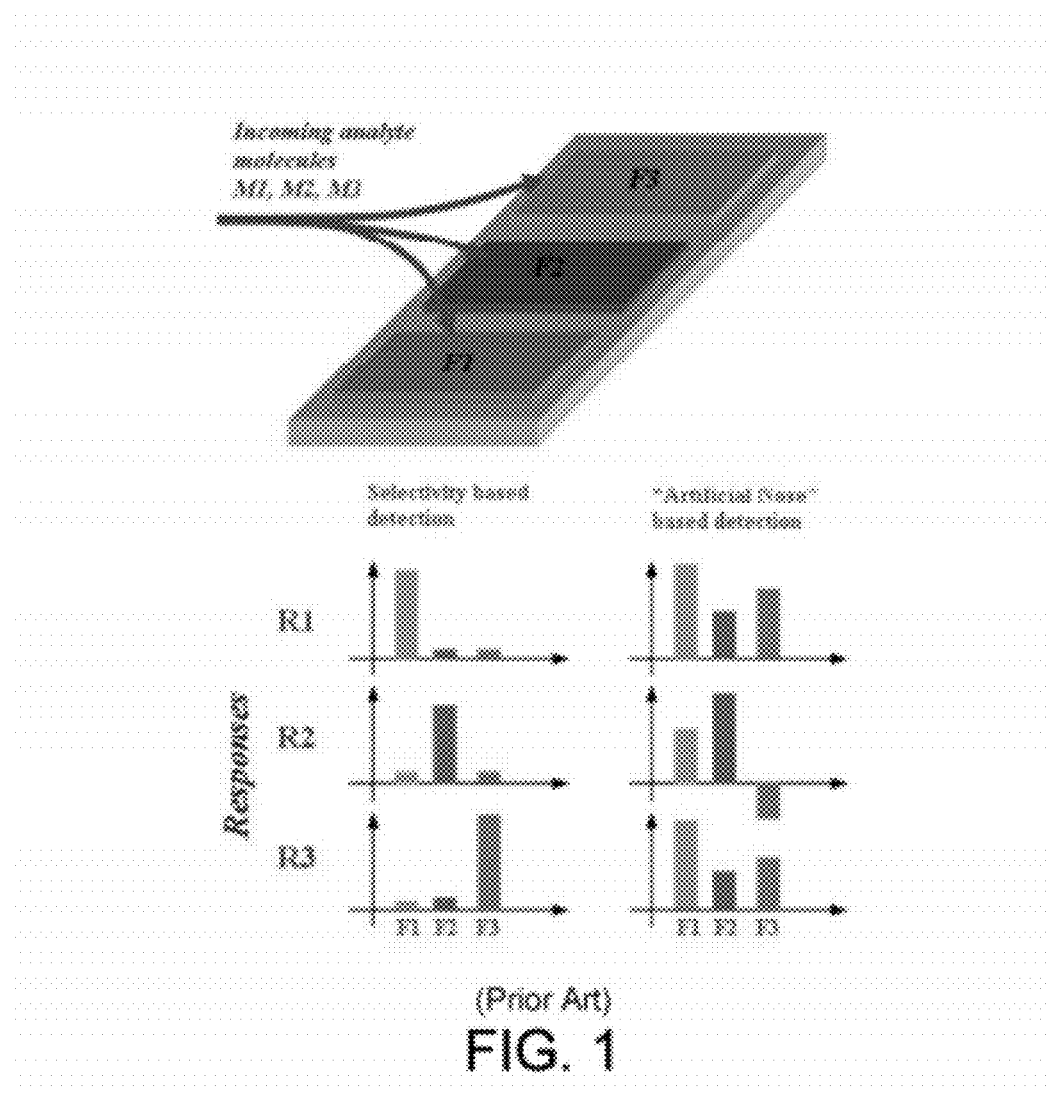
FIG. 1 shows a schematic diagram of the selectivity based and "Artificial nose" based detection strategies. Equal concentration of all molecular species has been assumed.
Figure 2:
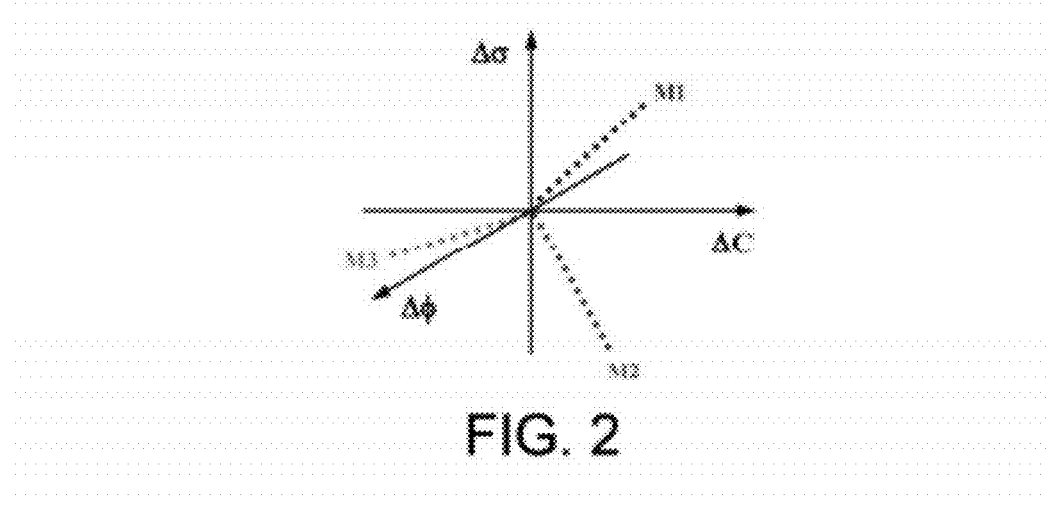
FIG. 2 shows unique gradients as signatures for molecules M1, M2, and M3.

The present invention is a multidimensional integrated detection and analysis system (MIDAS) for any gas or fluid that transfers or accepts electronic charge (including but not limited to $CH_4$, $CO_2$, CO, $NO_x$, $SO_x$, $H_2O$, $NH_3$, $NH_x$), MIDAS allows for the development of a highly sensitive, selective, and expedient sensor platform capable of uniquely identifying adsorbed molecules based on simultaneous measurement of truly orthogonal responses based on work function ($\phi$), capacitance (C), and/or conductance ($\sigma$) changes. These responses lead to a unique gradient in the 3-dimensional signature space as shown in FIG. 2. Advantages of MIDAS include: (i) accurate detection of any single molecular species and its concentration without a selective functionalization layer; (ii) determination of real-time signatures of target molecules, facilitating highly expedient detection and mixture analysis; (iii) vast improvement in overall sensitivity, response time, and false detection rate when applied to the sensing techniques discussed above.

The systems and methods of the present invention can employ a microcantilever based detection device. With the possibility of integration with Si based circuitry through standard fabrication processes, microcantilevers have emerged as very important micro-electromechanical sensing elements in the last decade. The microcantilevers, which resemble tiny diving boards, are extremely sensitive to a variety of physical factors including changes in temperature, pressure, surface stress, attached mass, and electrostatic, magnetic and van der Waals forces. This has facilitated the use of microcantilevers as transducer elements in a wide variety of sensing applications including the detection of chemical and bio-molecules. The current detection methodology used is almost exclusively based on the stress change of the cantilever and has been applied to the detection of a wide variety of molecules including organic vapors, explosives, and bio-molecules. However, it suffers from the disadvantage that the cantilever needs to be functionalized (to promote molecular adsorption), a process that is complicated and not very repeatable. In addition, the cantilever needs to be replaced whenever the functionalization layer degrades, which can be quite expensive in the longer run, especially for multi-cantilever systems. Therefore, it is highly desirable to have a detection technique that can work without functionalization of the cantilever.

In one particular embodiment, the microcantilever detection system for use in the present invention can include a microcantilever device positioned in working proximity to a sensing surface. By keeping the sensing surface separate from the microcantilever, the system can be reused simply by replacing or cleaning the separate sensing surface without the need for a new microcantilever device. Additionally, the sensing surface can be replaced (so as to refresh or to detect a different targeted analyte) without having to disturb the microcantilever device.

Specifically, the detection system of the present invention can utilize a non-contact microcantilever device. That is, the surface of the microcantilever (e.g., the surface of the resonating beam) does not bind or otherwise attach to an analyte or other chemical. Thus, the microcantilever device, including the resonating beam, can be kept in pristine condition during and even after repeated use. Additionally, through the use of a non-contact microcantilever device, there is no need to functionalize the surface of the resonating beam in a particular manner depending on the targeted analyte. Thus, there can be more uniformity in the manufacture of each microcantilever device. Suitable non-contact microcantilever devices are disclosed in international patent application Ser. No. PCT/US 2007/085615 filed on Nov. 27, 2007, the disclosure of which is incorporated herein by reference in its entirety.

Figure 9:
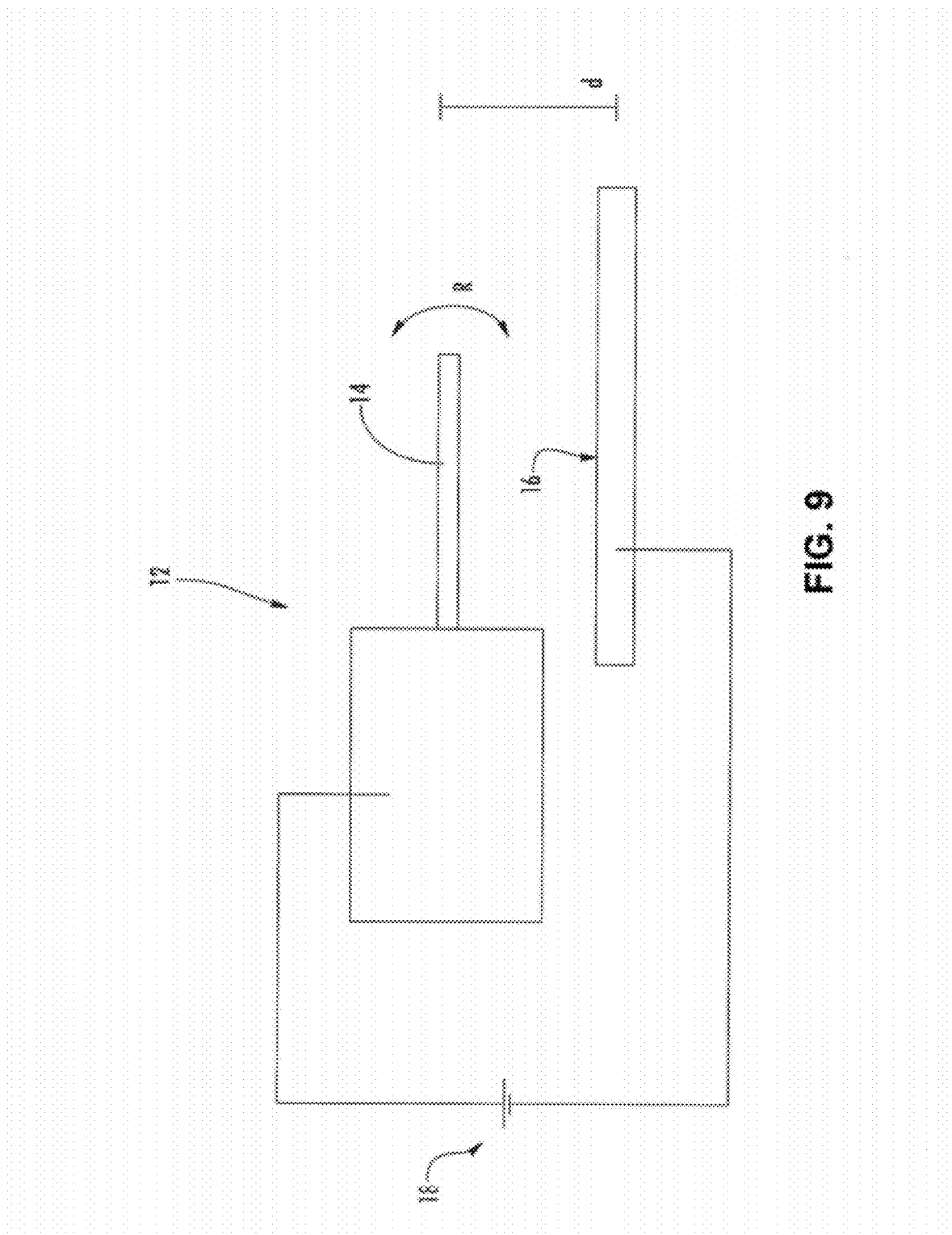
FIG. 9 shows a prospective view of an exemplary non-contact microcantilever detection system for use in the present invention.

Referring to FIG. 9, an exemplary detection system 10 is shown having a microcantilever device 12 with a resonating 14 and a sensing surface 16. Although shown as a resonating beam 14 having a rectangular shape, it should be understood that any other shaped resonating element can be utilized in accordance with the present invention. Both the microcantilever device 12 and the sensing surface 16 will be discussed in greater detail below.

As shown, the resonating beam 14 is positioned within working proximity (measured by the distance d) to the sensing surface 16, so as to induce a charge on the resonating beam 14 while remaining in a non-contact mode. The preferred gap distance between the sensing surface 16 and the resonating beam 14 can vary, and can depend, for instance, upon the nature of the atmosphere surrounding the system and on the geometric relationship between the microcantilever device 12 and the sensing surface 16. In general, however, the intervening distance between the resonating beam 14 and the sensing surface 16 can be at least enough so as to ensure no contact between the sensing surface 16 and the resonating beam 14 at resonance, while ensuring the capability of establishing a capacitance driven electrostatic force on the microcantilever device 12.

A voltage is applied to the detection system 10, so as to induce a modulated electrostatic force on the cantilever. The detection system 10 can also include a signal generator 18, shown as an ac voltage generator. The voltage applied to the sensing surface 16 can induce an electrostatic force on the resonating beam 14, which, at the appropriate parameters, can force the resonating beam 14 into resonance.

In FIGS. 9 and 10, the resonating beam 14 is positioned above the sensing surface 16 such that the resonating beam 14 and the sensing surface 16 are substantially parallel to each other. However, any other configuration (e.g., tip-to-tip) could be utilized in accordance with the present invention.

The microcantilever device 12 can include one or more micro-sized or nano-sized elements. For example, the devices can utilize one or more micro-sized beams, such as the resonating beam 14 shown in FIGS. 9-10. In general, micro-sized beams can be classified as those having micrometer dimensions, e.g., greater than about 1 micrometer (μm) in width and/or thickness. For example, micro-cantilevers of the present invention can have a length dimension less than about 500 μm, for instance between about 90 μm and about 350 μm and a width dimension less than about 50 μm, for instance between about 10 μm and about 50 μm. Nano-sized beams generally include those elements having width and/or thickness dimensions less than the micro-sized devices (e.g., less than about 1 μm). For instance, in one embodiment, nano-sized elements of the invention can have a width and/or thickness dimension less than about 500 nm. Nano-sized elements can, however, have a length in the micrometer range. For instance, one exemplary nano-cantilever of the invention can have a generally circular cross-section of between about 1 nm and about 200 nm in diameter, and a length in the micrometer range, for instance greater than about 5 μm.

The beams of the devices can have any geometric shape and can have an aspect ratio (L/D) greater than about two. Moreover, though much of the following discussion is directed to embodiments in which the beams are provided in a device as a cantilever, i.e., clamped at a first end and free to vibrate at a second end, the presently disclosed methods and devices are equally applicable to a beam provided in other orientations. For example, the invention is also directed to devices in which the disclosed beam is clamped at both ends, i.e., a double-clamped beam. In particular, the presently disclosed invention encompasses any micro- or nano-sized element that can be electrostatically driven into resonance.

The elements of the disclosed devices can generally be formed of any material including a suitable conductive or semi-conductive material at least at the surface of the element. For instance, in one embodiment, an element can be formed of a non-conductive base substrate that has been coated with a conductive outer layer. Fabrication materials and techniques for forming many structures suitable for use in the presently disclosed devices are generally known to those of ordinary skill in the art. For example, materials encompassed by the invention include metallic nanowires, gallium arsenide/aluminum arsenide structures, nanocrystalline diamond films, and materials based upon silicon including, but not limited to, silicon on insulator structures, silicon carbide on silicon structures, aluminum nitride on silicon structures, and amorphous silicon nitride structures.

In one embodiment, the elements of the disclosed devices can be nanostructures, and in one particular embodiment, carbon-based nanostructures. For example, carbon-based nano-cantilevers of the disclosed devices can be formed from nanotubes, including single-walled nanotubes (SWNT) and multi-walled nanotubes (MWNT), nanobelts, nanorods, nanowires, nanocoils, and the like. In addition, the elements can be formed of more than one nanostructure in combination, for example, a bundle of nanotubes, or a stack of nanobelts, or even combinations of two or more structures of different shapes. Nanostructures of the invention are not limited to carbon-based nanostructures, however, and nanostructures formed of other material can be utilized. For example, nanostructures etched from silicon or including any other suitable conductive or semi-conductive material at the surface can be utilized. In this respect, other resonating structures, such as beams attached at both ends can also be used for the non-contact detection.

In general, the elements of the disclosed devices can be formed according to any known formation method and of any suitable material. For example, carbon-based nano-cantilevers of the invention can be formed via physical evaporation methods such as vapor-liquid-solid (VLS) processes, chemical vapor deposition (CVD) methods, catalyst assisted processes, processes involving electric arc gas discharge, pulsed laser ablation techniques, or by simple mechanical abrasion, as are generally known to those of ordinary skill in the art.

In one particular embodiment, the microcantilever device can be positioned in a vacuum. By positioning the microcantilever device in a vacuum, any potential contact between the microcantilever and any environmental contaminants are avoided. Thus, false readings can be minimized. In addition, the quality factor of the resonance increases dramatically in vacuum (usually 100-1000 times) causing exceptional sensitivity toward molecules that can absorb on the functionalized surface outside of the vacuum enclosure.

The sensing surface can be constructed of any suitable material that has an affinity for the targeted analyte. One of ordinary skill in the art would be able to functionalize the sensing surface to attract and bind (e.g., via covelent bond, ionic bond, hydrogen bond, etc.) the targeted analyte(s).

Also, the sensing surface acts as a counter electrode to the microcantilever to complete the detection system circuit. Although the sensing surface itself may have only marginal conductivity, the sensing surface can be located on a more conductive material, such as a metal electrode or a semiconductor attached to an electrode. In one particular embodiment, the sensing surface can be applied on semiconductor substrate.

For example, when sensing nitrogen oxides, the sensing surface can be silicon or silicone oxide. Gases such as NOx (where x is 1 or 2), $NH_3$, and $H_2S$ have the property of releasing or accepting electrons when in contact with transition metal oxides, such as $In_2O_3$, $SnO_2$ and ZnO. In this embodiment, the reference electrodes (i.e. the counter electrode) can be coated with these materials, and the surface potential changes can be measured at room temperature and/or at elevated temperatures.

In another embodiment, the present inventors have discovered that the use of thin graphite films is suitable for sensing the above-mentioned gases. Thin films of graphite can be produced economically on a variety of substrates, including metals, semiconductors and insulators. As used herein, the term "graphite" is meant to encompass graphite in any form. In one particular embodiment, nanostructured graphite (NG) can be used as the functionalization layer, which can be deposited easily and inexpensively on a variety of substrates by simple mechanical abrasion on the substrate or by coating powders (comprising nanoscale particles) of graphite. The NG layer can mostly include of crystalline graphene films with nanoscale dimensions, creating a large surface area. This enormous surface area of the NG films leads to very high sensitivity, possibly much higher than continuous and fully crystalline graphene layers. The dimensions of the graphene sheets used in the functionalization layers can be controlled to enhance sensitivity. Graphene films, which consist of a single layer of carbon atoms are sensitive to a variety of molecules. For electron poor gases such as $NO_2$, detection down to a single molecular level is possible. Graphene is a unique material that is truly two-dimensional, and has electron and hole mobilities of several thousands at room temperature with carrier concentration reaching as high as mid $10^{13}$ cm$^{-2}$. A remarkable property of graphene is that it is ambipolar (both electrons and holes carry current simultaneously), with a slight overlap of a few tens of meV between the conduction and valence band edges. Therefore, it is relatively easy to make a few layer graphene (FLG) film p-type or n-type (holes or electrons as the net carriers) by applying appropriate bias between the graphene film and a metal electrode separated by an insulator (such as $SiO_2$). The bias dependent polarity of graphene presents a unique opportunity for sensing applications, since the adsorption of electron-rich and electron-poor molecules on a material surface is significantly influenced by p or n-type nature of the material.

The graphene sensing surface can be made by coating graphene layer onto a grounded substrate. The process used to create these films in this case is not (1) the more commonly used physical deposition using sputtering or pulsed laser deposition or even (2) the economically attractive chemical deposition technique, which lends itself to commercialization. The process used to create these films involves applying graphite (such as from a readily available pencil) onto a substrate such as metal or even paper. Of course, any method of applying graphite to form the sensing surface can be utilized.

In other embodiments, the sensing surface can include nanostructures, such as carbon-based nanostructures. The ability of carbon nanostructures to quickly adsorb materials is of benefit to the disclosed devices in certain sensing applications. For example, carbon-based sensing surfaces can be formed from nanotubes, including single-walled nanotubes (SWNT) and multi-walled nanotubes (MWNT), nanobelts, nanorods, nanowires, nanocoils, and the like. Nanostructures of the invention are not limited to carbon-based nanostructures, however, and nanostructures formed of other material can be utilized. For example, nanostructures etched from silicon or including any other suitable conductive (such as Pt or Pd nanoparticles for hydrogen sensing) or semi-conductive material at the surface can be utilized.

In one particular embodiment, nanostructured graphite (NG) can be used as a functionalization layer, which can be deposited easily and inexpensively on a variety of substrates. In one embodiment, the NG layer mostly can contain mostly crystalline graphene films with nanoscale dimensions, as characterized through TEM. The enormous surface area of the NG films leads to very high sensitivity, possibly much higher than continuous and fully crystalline graphene layers. The dimensions of the graphene sheets used in the functionalization layers can be controlled to enhance sensitivity. It has been shown very recently that graphene films, which consist of a single layer of carbon atoms (discovered to exist in a stable form under ambient conditions in 2004), are sensitive to a variety of molecules. For electron poor gases such as $NO_2$, detection down to a single molecular level is possible. Graphene is a unique material that is truly two-dimensional, and has electron and hole mobilities of several thousands at room temperature with carrier concentration reaching as high as mid $10^{13}$ cm$^{-2}$. A remarkable property of graphene is that it is ambipolar (both electrons and holes carry current simultaneously), with a slight overlap of a few tens of meV between the conduction and valence band edges. Therefore, it is relatively easy to make a few layer graphene (FSG) film p-type or n-type (holes or electrons as the net carriers) by applying appropriate bias between the graphene film and a metal electrode separated by an insulator (such as $SiO_2$). The bias dependent polarity of graphene presents a unique opportunity for sensing applications, since the adsorption of electron-rich and electron-poor molecules on a material surface is significantly influenced by p or n-type nature of the material.

Potentiometric Detection Technique

Figure 3:
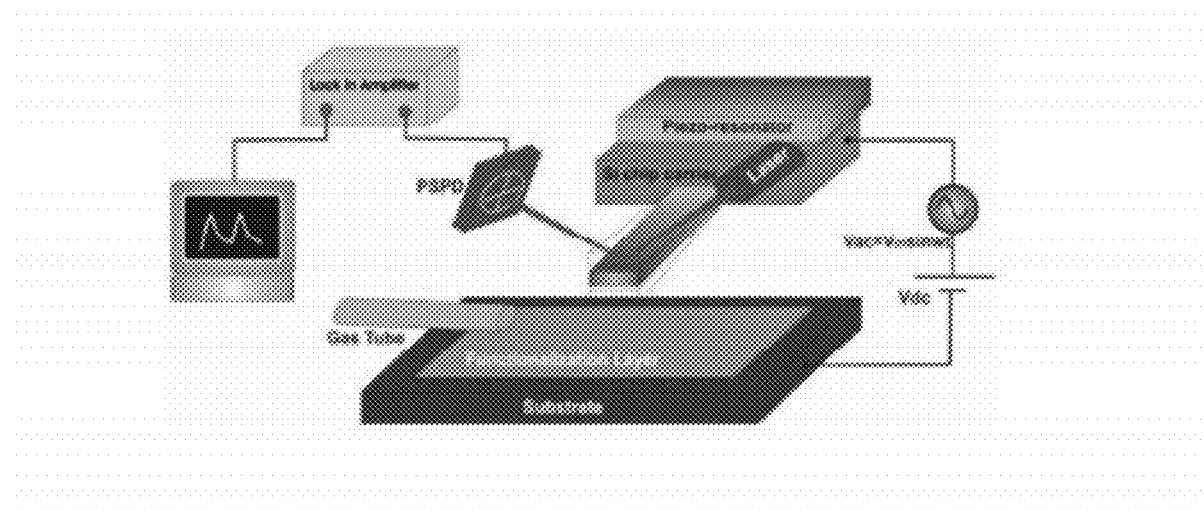
FIG. 3 shows a schematic diagram of the potentiometric detection technique using the current SPM based set up in ambient.

This technique, as an alternative to the stress change based technique, works on the basis of change in surface work function (SWF) due to molecular adsorption. Any change in surface work function causes a change in the electrostatic force between a resonant microcantilever and a reference electrode. Mathematically, the ω-component of the force $F_\omega$ is given as $F_\omega = \partial C/\partial z(V_{dc} - \Delta\phi)V_{ac}\sin\omega t$, where C and $\Delta\phi$ are the capacitance and work function difference between the cantilever and the reference electrode, $V_{dc}$ and $V_{ac}$ are the applied dc and ac biases, and z is the separation. The amplitude $a_0$ at resonance is given as:

$$a_0 = (Q/k)\partial C/\partial z(V_{dc} - \Delta\phi)V_{ac}\sin\omega t, \quad (1)$$

where Q and k are the quality factor and spring constant of the cantilever, respectively. A schematic of the potentiometric detection technique is shown in FIG. 3. The major advantages of the potentiometric detection are: (i) high sensitivity to changes in surface potential, which can be tuned easily by controlling $V_{ac}$ and z; (ii) it is a truly surface based technique, and therefore independent of the bulk material properties, resulting in a much lower response time; and (iii) for detection based on changes in SWF, the cantilever does not have to be functionalized but the substrate electrode can be functionalized instead. This is because only the relative work function change is important [Eq. (1)].

Phenomenon of Parametric Resonance (PR)

Figure 4:
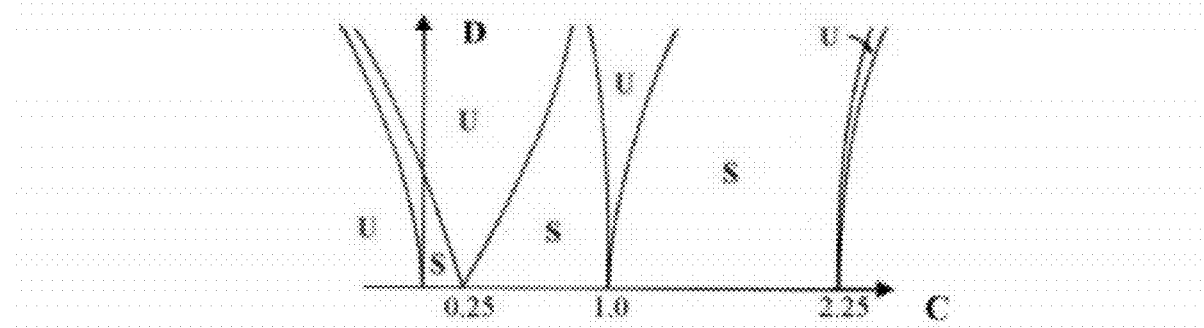
FIG. 4 shows a schematic diagram showing unstable (U) and stable (S) regions, where parametric resonance can be induced in oscillatory systems

As mentioned above, the quality factor of a resonant microcantilever decreases in air compared to vacuum, which significantly reduces the SWF sensitivity of the cantilever. It is possible to increase the sensitivity of the microcantilever to SWF changes by inducing PR, in a way similar to recent demonstrations of mass sensitivity improvement by 1-2 orders of magnitude compared to normal resonance. The major advantage of PR in comparison to normal resonance is that the effect of damping in reducing the quality factor is insignificant. The phenomenon of PR has been described in detail in X. M. H. Huang, M. Manolidis, S. C. Jun, and J. Hone, "Nanomechanical hydrogen sensing," Appl. Phys. Lett. 86, 143104 (2005), which is incorporated by reference herein. The general behavior of an oscillatory system undergoing PR is described by non-linear Mathieu equation $$\ddot{x} + A\dot{x}(C + D\sin\omega t)x = 0 \quad (2)$$

where x denotes the displacement of the system from the mean position, and $D\sin\omega t$ denotes the periodic variation of the "parameter" as a function of time. For observation of parametric resonance, the system should be in the unstable "tongue" region of the instability that occurs for $C = n^2/4$, $n = 1, 2, 3 \ldots$. The regions of instability can be mapped in the C-D plane and are shown schematically in FIG. 4. This result also implies that the frequencies of excitation at which parametric resonance occurs are given as $$f = 2f_0/n, n = 1, 2, 3 \ldots, \quad (3)$$

where $f_0$ is the natural frequency of oscillation. For microcantilevers, the motion under parametric resonance can also be described by Eq. (2), where $$C = \frac{k}{m\omega_0^2} - \frac{1}{2}\frac{\varepsilon_0 A V_0^2}{md^3\omega_0^2},$$

and $$D = \frac{\varepsilon_0 A V_0^2}{4md^3\omega_0^2},$$

$V_0$ is the applied ac voltage, A, k and m are the area, spring constant, and mass of the cantilever, and d is the distance. The expressions for C and D will be modified slightly if there is a dc voltage also applied to the system. However, it can be observed that for certain ac and dc bias, the cantilever's frequency can be at the boundary of the unstable zone near each frequency defined by Eq. (3). At the boundary, the cantilever oscillation will be extremely sensitive to very small changes in dc bias (which can also occur due to work function changes), which can dramatically change the stability (manifested as a change in amplitude) of the system. In one embodiment of the present invention, parametric resonance is examined in conjunction with the potentiometric detection technique to detect changes in surface work function with very high sensitivity.

Capacitive Detection Technique

The capacitive detection technique is based on the change in capacitance between a functionalization layer and an electrode, caused by a change in dielectric constant due to polarization of adsorbed molecules under an applied electric field. Although not as popular as the amperometric detection techniques, the capacitive detection technique can be very useful for very fast and highly sensitive detection for a large number of molecules as recently demonstrated by Snow et al. They used an electrically continuous CNT network as the functionalization layer deposited on a $SiO_2/Si$ substrate for detection. The fringing field from the CNTs resulted in molecular polarization leading to a change in dielectric constant which is given by Clausius-Mossotti equation, $$\varepsilon = 1 + 4\pi \frac{N\gamma}{1 - (4\pi/3)N\gamma} \quad (4)$$

Figure 5:
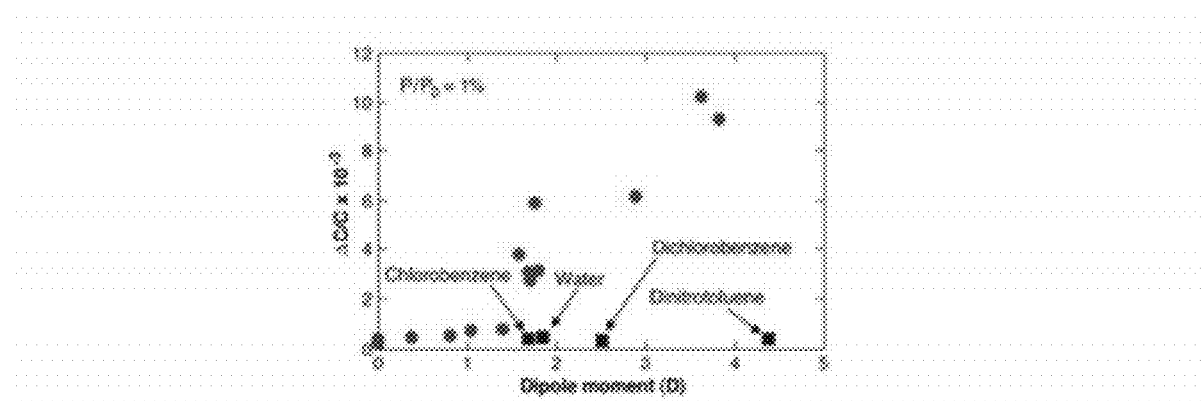
FIG. 5 shows measured capacitance response versus molecular dipole moment.

Here, N is the number of molecules, and $\gamma$ is the polarizability given as $\gamma = \gamma_{mol} + (\mu^2/3kT)$, and $\mu$ is the dipole moment. The first term arises due to intrinsic polarizability, and the second term due to field-induced alignment of otherwise randomly oriented molecular dipoles. FIG. 5 shows a plot of $\Delta C/C$ versus $\mu$ for a number of analyte molecules for the same partial pressure $P/P_0=1\%$. We observe a general trend for $\Delta C/C$ proportional to $\mu^2$, although deviation for aromatic compounds and water is observed, which has been attributed to these molecules lying flat on the CNT surface. A major advantage of the capacitive detection technique is that it is dependent only on the surface properties just like SW F, and fully compatible with cantilever based measurements (discussed later), enabling easy integration into the MIDAS sensing platform.

Simultaneous Measurements of Multiple Parameters

As mentioned earlier, sensors based on one dimensional response cannot simultaneously determine the nature of the species, as well as its concentration, since both of them affect the parameter that is measured (such as conductance). The advantage of a simple two parameter, or more, (e.g., such as two of work function $\phi$, conductance $\sigma$, or capacitance C) measurement is that the nature of the molecules as well as the concentration can be determined.

In one particular embodiment, both the work function and the conductance of the microcantilever device can be measured to determine the nature of the analyte. These measurements can be normalized by proportioning the measurement to the change in current ($\Delta I/I$). The dependence of $\phi$ or $\sigma$ on the number of molecules N that is added to the surface can then be eliminated by taking the ratio of the two parameters. Mathematically, the surface barrier $\phi(t)$ and conductance $\sigma(t)$ at any instant in the presence of target molecular species M1 under ambient is given as:

$$\phi(t)=\phi_{10}x(t)+\phi_{00}[1-x(t)] \text{ and, } \sigma(t)=\sigma_{10}x(t)+\sigma_{00}[1-x(t)] \quad (5)$$

where $\phi_{00}(\sigma_{00})$ and $\phi_{10}(\sigma_{10})$ are the respective surface work functions (conductivities) when the surface is in equilibrium under ambient conditions, and under maximum possible coverage with M1, and x(t) is the surface coverage by M1 at any given instant. Rearranging, we have $$\phi(t)-\phi_{00}=(\phi_{10}-\phi_{00})x(t) \Rightarrow \Delta\phi(t)=\Delta\phi_{10}x(t),$$

$$\sigma(t)-\sigma_{00}=(\sigma_{10}-\sigma_{00})x(t) \Rightarrow \Delta\sigma(t)=\Delta\sigma_{10}x(t) \quad (6)$$

Now, taking a simple ratio of the work function and the conductivity changes, we can eliminate the time dependent coverage, and obtain unique signature of M1 [$=\Delta\phi(t)/\Delta\sigma(t)$]. However, any residual occupation of the states by M1 or some molecule that has higher binding energy than M1 (and will not likely be replaced by M1) will change $\phi_{00}$ and $\sigma_{00}$. Then the simple ratio will not be useful to extract the signature, and we have to obtain the ratio of the slopes $d\Delta\phi(t)/dt$ and $d\Delta\sigma(t)/dt$, which is actually equal to $d\Delta\phi(t)/d\Delta\sigma(t)$, to eliminate any effect of the fixed occupied states and obtain the signature. Thus, this technique can not only uniquely identify the target molecules, but also can do so even when the functionalization layer surface is not fully reset. In addition, detection is possible within a very short time without having to wait for the steady state values. For mixture analysis of two molecular specie M1 and M2, there are three variables involved, their respective natures and their ratio R. The three governing equations for this case will be: $\Delta\phi(t)=\Delta\phi_{10}x(t)+\Delta\phi_{20}y(t)$, $\Delta\sigma(t)=\Delta\sigma_{10}x(t)+\Delta\sigma_{20}y(t)$, and $\Delta C(t)=\Delta C_{10}x(t)+\Delta C_{20}y(t)$, which can be solved to find the ratio as well as the two types of molecules involved. Thus using simultaneous measurements of surface work function, conductance, and capacitance changes, mixture analysis is possible without using any functionalization layer. This technique when used in conjunction with the Artificial Nose or the selectivity based detection techniques, can result in much faster detection with dramatically reduced false detection rate.

Examples to Illustrate Present Invention

Figure 6:
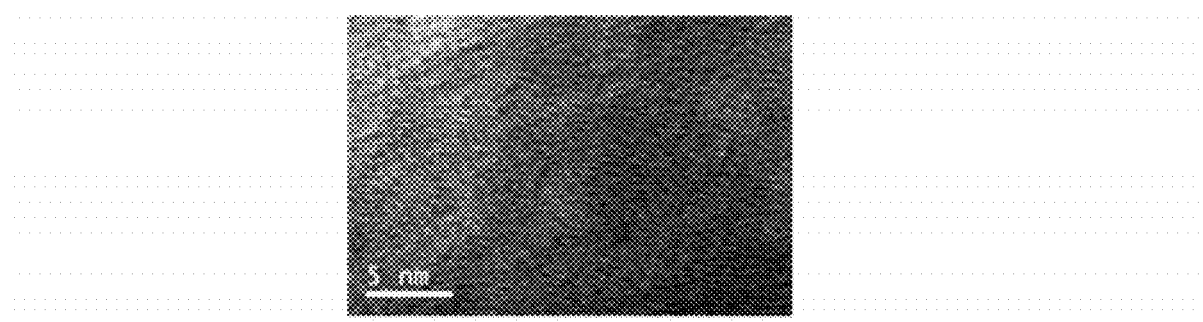
FIG. 6 shows an HRTEM image showing mixed amorphous (A) and crystalline (C) phases, with the later being predominant.

The present invention is a very easy and inexpensive way of depositing the NG functionalization layer by simple mechanical exfoliation (abrasion) on a ceramic substrate (metallic plates or even paper could also be used). The nanostructures were characterized by TEM to understand their structure. FIG. 6 shows the lattice resolved TEM images of a graphite nanostructure. We found that the NG consists mostly of crystalline graphene sheets, although some amorphous phases are also intermixed. Very good repeatability can be observed for surface potential over different cycles. Very high rise rates are observed (>1 mV/s for 1.5 ppm $NO_2$) which can allow $NO_2$ detection in tens of ms timeframe for any concentration over 1 ppm assuming a background noise of ~50 μV. The noise limited detection limit of the current set up is estimated to be a few ppb which is comparable to the lowest detection limits of $NO_2$ reported in the recent literature. As mentioned earlier, the response time and the sensitivity are expected to improve further in a more optimized configuration using the STB. Sensing experiments with highly oriented pyrolytic graphite resulted in much lower detection sensitivity. The enormous surface area of NG is responsible for the extremely high sensitivity of NG.

Simultaneous Potentiometric and Amperometric Measurements

Figure 7:
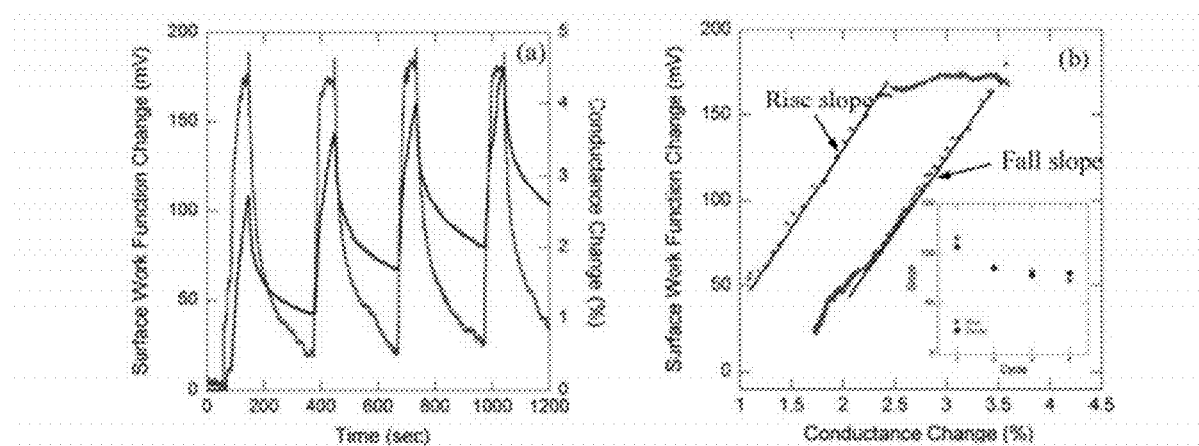
FIG. 7 shows (a) simultaneously measured SWF and conductance changes for 9 ppm $NO_2$ and (b) SWF vs. conductance changes for the $2^{nd}$ cycle. The inset shows the rise and fall slopes for all the cycles.
Figure 8:
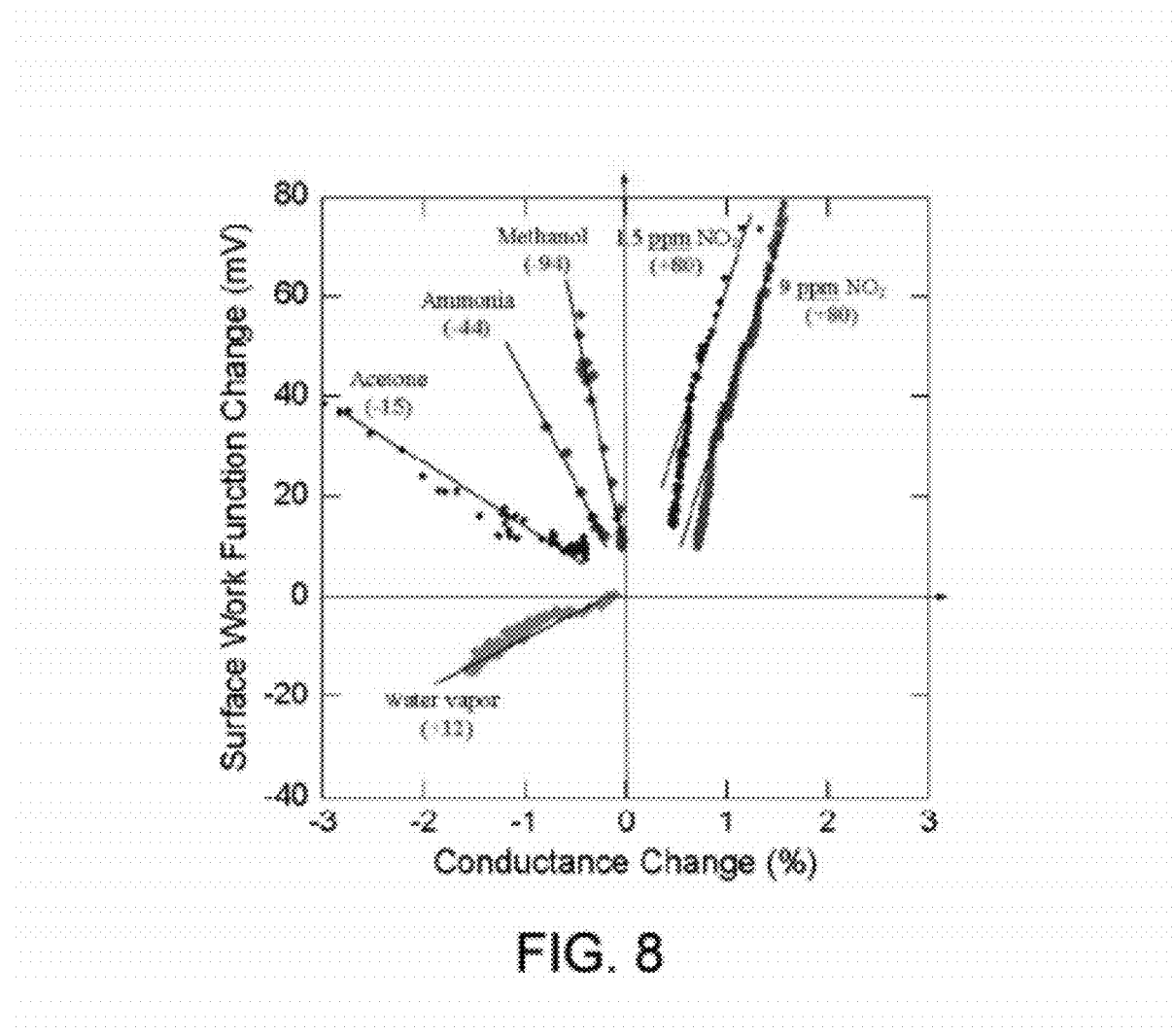
FIG. 8 shows two dimensional signatures of common analyte molecules, and different concentrations of $NO_2$.

Simultaneous measurements of surface work function and conductance transients were carried out with NG coated ceramic substrates. FIG. 7 (a) shows simultaneously measured transients for SWF and conductance changes (proportional to $\Delta I/I$) when 8 ppm $NO_2$ flow is switched on and off. The SWF changes for different cycles are very similar and fast, while the conductivity transients are slower and show an upward shift for the peaks and valleys. This is because the SWF changes only due to adsorption and desorption at the surface which is a much quicker process compared to the conductance change that occurs due to diffusive adsorption and desorption processes that extend over a significant thickness of the porous NG film. We expect that this difference in response time can be eliminated by using thinner functionalization layers. As pointed out above, it is possible to use the derivative of SWF change ($\Delta\phi$) and conductance change ($\Delta G$), $d\Delta\phi/d\Delta G$, to uniquely identify the adsorbed molecular species. The concentration can be obtained from either the rate of change of the parameters or their final saturated value. SWF change ($\Delta\phi$) plotted against conductance change ($\Delta G$) for the $2^{nd}$ cycle is shown in FIG. 7(b). The rise and fall slopes for all the cycles are shown in the inset which are found to be almost exactly equal, as expected from theory. As we can see, except for the first cycle, the rise and fall slopes vary within a narrow range of 75-85 mV per percent change in conductance. To verify whether the slopes can be used as a reliable parameter to differentiate between different molecular species, we measured the responses for ammonia, water vapor, methanol, and acetone. FIG. 8 shows two-dimensional signatures for several common molecules as well as for different concentrations of $NO_2$. We find almost identical slopes for 9 and 1.5 ppm $NO_2$, however, very different signatures are observed for different molecules, which is indeed remarkable and quite surprising. This exciting result is the first indication that it is possible to extract unique signatures of the molecules based on two and three-dimensional measurements. We have noticed that the initial ratios can differ from the later ratios that are unique, and remain constant, which will be investigated further. The concentration can be obtained from the initial rise rates for the SWF, which has been observed to monotonically increase with concentration.

The foregoing description of the invention and examples along with other modifications and variations to the present invention may be practiced by those of ordinary skill in the art, without departing from the spirit and scope of the present invention. In addition, it should be understood that aspects of the various embodiments may be interchanged both in whole or in part. Any experiments are provided to illustrate the present invention and are not intended to limit the scope of the invention. Furthermore, those of ordinary skill in the art will appreciate that the foregoing description is by way of example only, and is not intended to limit the invention.

What is claimed:

1. A method of identifying an analyte using multi-dimensional analysis with a microcantilever detection device, the method comprising
    applying a current to the microcantilever detection device, wherein the microcantilever detection device comprises a resonating element positioned within working proximity to a sensing surface on a counter electrode, wherein the current provides an initial surface work function, an initial conductance, and an initial capacitance;
    exposing the microcantilever detection device to an analyte so that the analyte binds to or reacts with the sensing surface to create a change in the surface work function (SWF), conductance, and/or capacitance of the microcantilever detection device;
    measuring the change in the SWF, conductance, and/or capacitance of the microcantilever detection device upon contact of the sensing surface with the analyte;
    plotting the change of the SWF with the change of conductance and/or capacitance of the microcantilever detection device, wherein the plot provides data to identify the analyte.

2. The method as in claim 1, wherein the change in the SWF and the change in the conductance and/or capacitance is normalized by proportioning the measurement to the change in the current ($\Delta I/I$).

3. The method as in claim 2, wherein the change in two parameters are measured, the two parameters being SWF and conductance.

4. The method as in claim 1, wherein plotting the measured change of the two parameters results in an extrapolated line that forms a signature for a particular analyte.

5. The method as in claim 4, wherein the extrapolated line can be compared to known signatures of known analytes to identify the analyte.

6. The method as in claim 1, wherein the plot defines an x-axis and a y-axis, wherein the x-axis represents the change in conductance and the y-axis represents the change in SWF.

7. The method as in claim 1, wherein plotting the change in the SWF, conductance, and capacitance of the microcantilever detection device results in creating a three-dimensional plot.

8. The method as in claim 7 further comprising:
    normalizing the measured change in SWF, conductance, and capacitance of the microcantilever detection device by proportioning the measurement to the change in the current ($\Delta I/I$).

9. The method as in claim 1, wherein the sensing surface comprises a layer of graphite.

10. The method as in claim 1, wherein the sensing surface comprises a nano structure.

11. The method as in claim 10, wherein the nanostructure comprises a carbon nanostructure.

12. The method as in claim 1, wherein the microcantilever detection device comprises a laser and photodetector based transduction mechanism.

13. The method as in claim 1, wherein the microcantilever comprises a piezo-resistive cantilever, and wherein the detection device measures the resistance of the piezo-resistive cantilever to detect the change in deflection of the cantilever caused by a change in surface potential.

14. The method as in claim 1, wherein the analyte comprises $NO_x$, where x is 1 or 2, $NH_3$ or $H_2S$.

15. The method as in claim 14, wherein the sensing surface $In_2O_3$, $SnO_2$ and ZnO.

16. The method as in claim 14, wherein the modified sensing surface comprises thin graphite film.

17. The method as in claim 16, wherein the thin graphite film comprises nanostructured graphite (NG).

* * * * *